US009097910B2

(12) United States Patent
Ogi et al.

(10) Patent No.: US 9,097,910 B2
(45) Date of Patent: Aug. 4, 2015

(54) IMAGING APPARATUS, DETECTING APPARATUS, AND IMAGING METHOD (75) Inventors: Hiroshi Ogi, Kyoto (JP); Satoshi Takahashi, Kyoto (JP); Yoshiki Umemoto, Kyoto (JP)

(73) Assignee: SCREEN Holdings Co., Ltd. (JP)

( * ) Notice: Subject to any disclaimer, the term of this patent is extended or adjusted under 35 U.S.C. 154(b) by 429 days.

(21) Appl. No.: 13/557,417

(22) Filed: Jul. 25, 2012

(65) Prior Publication Data

US 2013/0076897 A1 Mar. 28, 2013

(30) Foreign Application Priority Data

Sep. 27, 2011 (JP) ................. 2011-210555

(51) Int. Cl.
*H04N 7/18* (2006.01)
*G02B 21/36* (2006.01)
*G01N 21/64* (2006.01)
*G02B 21/16* (2006.01)

(52) U.S. Cl.
CPC .......... *G02B 21/365* (2013.01); *G01N 21/6428* (2013.01); *G02B 21/16* (2013.01); *H04N 7/18* (2013.01)

(58) Field of Classification Search
CPC ................. G06K 9/00127; G06T 2207/30024; G06T 7/0012; G02B 21/34; G02B 21/36; B01L 3/5085; B01L 2300/0829; H04N 7/18; G01N 21/6428; G01N 21/645
USPC ............. 348/79, 143; 382/133, 134; 359/368, 359/369, 396, 398; 435/288.4; 422/82.08, 422/82.05
See application file for complete search history.

(56) References Cited

U.S. PATENT DOCUMENTS

| 5,233,668 | A  | * | 8/1993  | Yokomori et al. ............. 382/134 |
| 5,234,665 | A  | * | 8/1993  | Ohta et al. ...................... 422/73 |
| 6,947,583 | B2 |   | 9/2005  | Ellis et al. ..................... 382/128 |
| 7,050,620 | B2 |   | 5/2006  | Heckman ...................... 382/133 |
| 7,120,282 | B2 |   | 10/2006 | Langan ......................... 382/128 |
| 7,129,473 | B2 |   | 10/2006 | Ishihara et al. ............... 250/234 |
| 7,190,818 | B2 |   | 3/2007  | Ellis et al. ..................... 382/128 |
| 7,262,858 | B2 |   | 8/2007  | Lin et al. ...................... 356/445 |
| 7,283,654 | B2 |   | 10/2007 | McLain ......................... 382/128 |
| 7,516,934 | B2 |   | 4/2009  | Chu et al. ...................... 248/550 |

(Continued)

FOREIGN PATENT DOCUMENTS

| JP | 04168346 | A | * | 6/1992 |
| JP | 05133904 | A | * | 5/1993 |

(Continued)

OTHER PUBLICATIONS

Japanese Office Action dated Apr. 22, 2014 for corresponding Japanese Patent Application No. 2011-210555 (3 pages).

*Primary Examiner* — Michael Lee
(74) *Attorney, Agent, or Firm* — Ostrolenk Faber LLP (57) ABSTRACT As light is allowed to impinge from above a microplate M and an imaging unit 13 (a line sensor 131 and an imaging optical system 132), which moves in a scanning motion along the bottom surface of the microplate M, receives transmitted light, images of wells W formed in the microplate M are captured. The scope of imaging by the line sensor 131 is greater than the diameter of at least one well W, or preferably, encompasses a plurality of wells. When the depth of field of the optical system 132 is 0.6 mm or less, the influence of reflection of side walls of the wells upon the images is reduced.

8 Claims, 8 Drawing Sheets

(56) References Cited

U.S. PATENT DOCUMENTS

| | | | |
|---|---|---|---|
| 7,582,415 B2 | 9/2009 | Straus | 435/4 |
| 7,718,131 B2 | 5/2010 | Jiang | 422/82.08 |
| 8,135,203 B2 | 3/2012 | Takagi et al. | 382/133 |
| 2010/0025567 A1 | 2/2010 | Lueerssen | 250/205 |

FOREIGN PATENT DOCUMENTS

| | | |
|---|---|---|
| JP | 06148066 A * | 5/1994 |
| JP | 2004-514920 | 5/2004 |
| JP | 2007-500344 | 1/2007 |
| JP | 2008-064534 | 3/2008 |
| JP | 2008-112190 | 5/2008 |
| JP | 2009-002674 | 1/2009 |
| JP | 2009-524801 | 7/2009 |
| JP | 2010-142768 | 7/2010 |
| JP | 2010-268723 | 12/2010 |
| WO | WO 01/84209 | 11/2001 |
| WO | WO 02/37158 | 5/2002 |
| WO | WO 2005/012880 | 2/2005 |
| WO | WO 2007/087183 | 8/2007 |

* cited by examiner

FIG. 6A : ORIGINAL IMAGE

FIG. 6B : BACKGROUND IMAGE

FIG. 6C : BINARIZED IMAGE

FIG. 7

| TYPES OF PARAMETER | SYMBOL | SIZE (UNIT mm/F-NUMBER IS DIMENSIONLESS) | | | |
|---|---|---|---|---|---|
| | | EXEMPLARY STRUCTURE 1 | EXEMPLARY STRUCTURE 2 | EXEMPLARY STRUCTURE 3 | EXEMPLARY STRUCTURE 4 |
| PIXEL PITCH OF LINE SENSOR | $\delta$ | 0.002625 | 0.0105 | 0.0105 | 0.0105 |
| EFFECTIVE LENGTH OF LINE SENSOR | w | 28.35 | 28.35 | 28.35 | 28.35 |
| FOCAL LENGTH | f | 58.63 | 95 | 95 | 95 |
| APERTURE VALUE (F-NUMBER) | F | 6.0 | 5.6 | 4.0 | 2.8 |
| DISTANCE BETWEEN PRINCIPAL POINT AND LINE SENSOR | s | 73.82 | 190 | 190 | 190 |
| DISTANCE BETWEEN PRINCIPAL POINT AND IMAGING TARGET (BOTTOM SURFACE OF WELL) | t | -289.44 | -190 | -190 | -190 |
| DEPTH OF FIELD | Dof | 0.612 | 0.235 | 0.168 | 0.118 |
| FIELD OF VIEW | w' | 111.16 | 28.35 | 28.35 | 28.35 |

FIG. 8A

| DEPTH OF FIELD [μm] | DETECTION ERROR COUNT (PIECE) | ERROR RATIO (%) |
|---|---|---|
| 612 | 29.7 | 1.42 |
| 235 | 0.3 | 0.02 |
| 168 | 0.0 | 0.00 |
| 118 | 0.0 | 0.00 |

FIG. 8B

IMAGING APPARATUS, DETECTING APPARATUS, AND IMAGING METHOD

CROSS REFERENCE TO RELATED APPLICATION

The disclosure of Japanese Patent Application No.2011-210555 filed on Sep. 27, 2011 including specification, drawings and claims is incorporated herein by reference in its entirety.

BACKGROUND OF THE INVENTION

1. Field of the Invention

The present invention relates to a technique for imaging of a sample plate which comprises a plurality of wells which contain a fluid or the like. The term "fluid or the like" used herein is a general term for liquids, gel-like or semi-fluid solid bodies and substances which are introduced into the wells as they are fluid and which thereafter harden.

2. Description of the Related Art

In medical or life science experiments, a fluid or the like (e.g., a culture fluid) is for example poured into each one of many depressed parts called wells which are arranged in a plate-like device, and cells or the like cultured in the fluid or the like are observed. Such a device is called, for example, a microplate or a microtiter plate. For example, in the process of developing an anticancer drug, a multitude of samples obtained by causing various drugs to act on cells at different densities are observed and the life and death of the cells are judged. Various optical devices for supporting such observations have been conventionally proposed.

For example, in an optical apparatus disclosed in the description of U.S. Pat. No. 7,718,131, wells are imaged by irradiating light from above the wells and receiving light transmitted to a lower side. In this technology, an image of one well is reformed from a plurality of partial images imaged while light is irradiated in different manners to cope with a problem that the shadow of a side wall surface of the well is reflected on an image due to the incidence of light focused by a lens.

Since it takes time to perform imaging of one well according to the conventional technique mentioned above, long time is necessary to obtain an image of an entire plate which comprises a number of wells. Over the recent years in particular, a plate with a hundred or more wells has been put into use, and it has become necessary to perform imaging of these many wells at a high measurement accuracy and at a high speed. However, the conventional technique mentioned above cannot meet the requirement sufficiently.

SUMMARY OF THE INVENTION

The invention has been made in light of the problem described above. Accordingly, the object of the invention is to provide a technique for performing imaging of each one of a plurality of wells which are formed in a sample plate at a high measurement accuracy and at a high speed.

To achieve above object, an aspect of the present invention is an imaging apparatus for imaging a sample plate whose surface has a plurality of wells which are capable of holding a fluid, comprising: an illumination member which irradiates light from above the sample plate which is in a horizontal condition; and an imager member which receives transmitted light which is transmitted to below the sample plate and captures an image which includes at least one of the wells, wherein the imager member includes an imaging element and an optical system which focuses the transmitted light upon the imaging element, and a depth of field of the optical system is equal or smaller than 0.6 mm.

As described in detail later, according to the findings obtained by the inventors of the invention, as imaging is performed with the transmitted light from the sample plate impinging upon the imaging element via the optical system which has the depth of field of 0.6 mm or less, images less affected by the shadows of the side walls of the wells are obtained. To be more specific, the density of the shadows of the side walls of the wells is reduced to an extent not influencing observation. This is significantly effective for imaging under an imaging condition according to which one or a plurality of wells as a whole is included in the scope of imaging. In short, with this configuration according to the invention, it is possible to perform imaging of the wells at a high measurement accuracy and at a high speed.

A detecting apparatus according to another aspect of the invention comprises: an imager part which has a same structure as that of the imaging apparatus described above; and a detector part which detects a specific section, which is contained in a liquid-state or solid-state culture medium which is held in the well and which exhibits a different optical characteristic from a culture medium, based upon an image captured by the imager part. With this configuration according to the invention, the influence of the side walls of the wells is suppressed in the captured images of the wells, and the specific section in the culture medium can be efficiently detected from such images. More specifically, the culture medium and the specific section appear differently from each other in the images due to the different optical characteristics of the culture medium and the specific section, and therefore, utilizing the different optical characteristics, it is possible to discriminate and detect the specific section within the images. In a detecting apparatus used in the field of medical treatments or life science for instance, a cell or a cell clump in the culture medium, a virus or the like corresponds to the "specific section." The invention is preferably applicable to a technique for detecting such a specific section contained in the culture medium which is held inside the wells. The "culture medium" referred below means a substance in the liquid or solid state which is held inside the wells, and the liquid-state culture medium may be expressed as a "culture fluid" as needed.

The other aspect of the invention is an imaging method of imaging a sample plate which has a plurality of wells which hold a liquid-state or solid-state culture medium, comprising the steps of: irradiating light from above the sample plate which is in a horizontal condition; and capturing an image containing at least one of the wells by an imaging element while the optical system focuses a light transmitted to below the sample plate upon the imaging element, wherein a depth of field of the optical system is equal to or smaller than 0.6 mm. With this configuration according to the invention, it is possible to perform imaging of the wells at a high measurement accuracy and at a high speed as in the case of the imaging apparatus described above.

According to the invention, it is possible to perform imaging of one well or a plurality of wells formed in the sample plate at a high measurement accuracy and at a high speed while suppressing the influence of the side walls of the wells.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DETAILED DESCRIPTION OF THE PREFERRED EMBODIMENTS

Figure 1A:
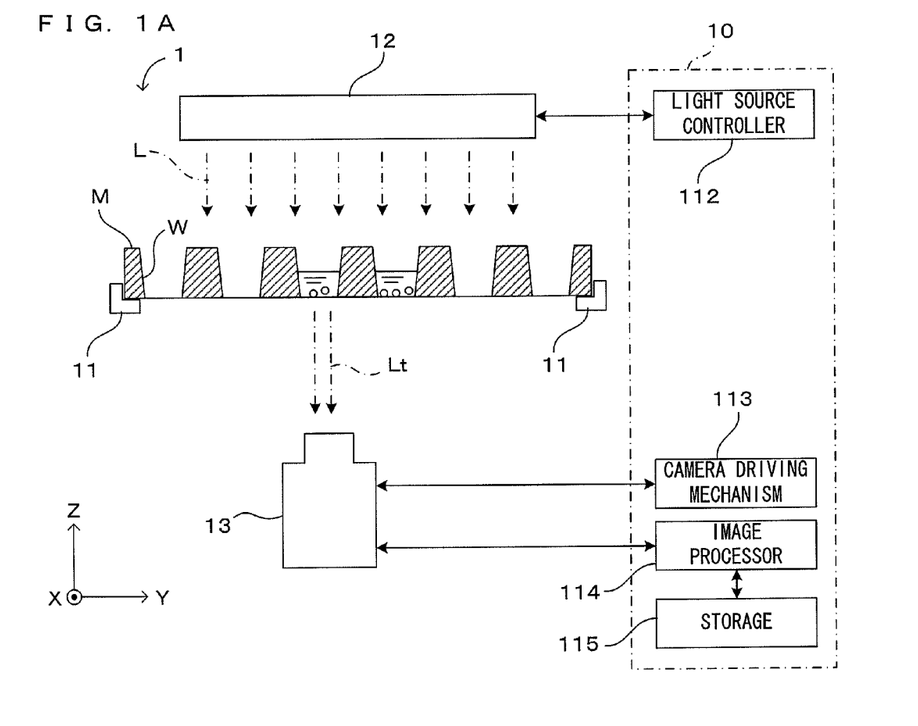
FIGS. 1A and 1B are diagrams which show schematic constructions of one embodiment of an imaging apparatus to which this invention is applied.
Figure 1B:
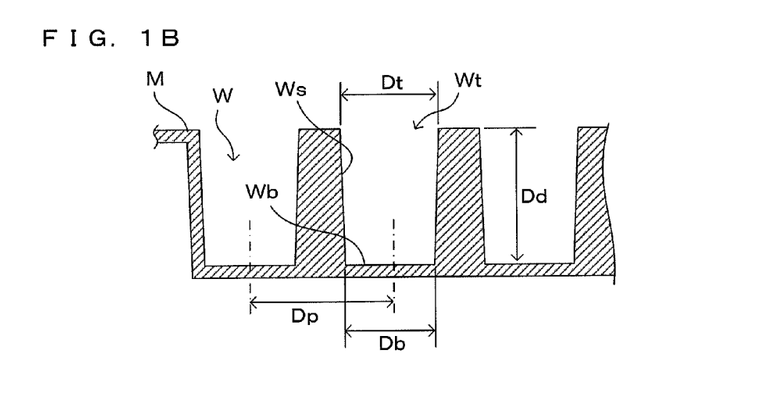

FIGS. 1A and 1B are diagrams which show schematic constructions of one embodiment of an imaging apparatus to which this invention is applied. As shown in FIG. 1A, this imaging apparatus 1 includes a holder 11 holding a sample (microplate) M formed with a plurality of, e.g. 96 (12×8 matrix array) wells W, into each of which a fluid such as a culture fluid, a culture medium or a reagent (only partly shown) is poured, in a substantially horizontal state by being held in contact with a peripheral edge part of the lower surface of this microplate M, a light source 12 provided above the holder 11, an imaging unit 13 provided below the holder 11, and a control unit 10 for performing a predetermined operation by controlling these. Coordinate axes are set as shown in FIG. 1A for the following description. An X-Y plane is a horizontal plane and a Z axis is a vertical axis.

The diameter and depth of each well W in the microplate M are typically about several mm. As an example, dimensions of each part of the microplate M used in experiments by the present inventors are shown. As shown in FIG. 1B, a diameter Dt of an opening Wt in an upper part of each well W is 6.69 mm, whereas an inner diameter Db of a well bottom surface Wb is 6.58 mm. As can be understood from these, an inner wall surface Ws of the well W is not a simple cylindrical surface, but an obliquely inclined tapered surface. Further, a depth Dd of the well W is 10.9 mm, and an arrangement pitch Dp of a plurality of wells W is 9 mm. Note that the dimensions of the respective parts are only examples and the dimensions of the microplate to be imaged by this imaging apparatus 1 are not limited to these, but arbitrary.

The light source 12, which is controlled by a light source controller 112 provided in the control unit 10, irradiates light L to a plurality of wells W at once from above the microplate M held on the holder 11 in response to a control command from the light source controller 112. Light to be irradiated is visible light, particularly preferably white light.

The imaging unit 13 functions as a camera for imaging an image of the microplate M by receiving transmitted light Lt emitted from the light source 12 and transmitted to a side below the microplate M. The imaging unit 13 is connected to a camera driving mechanism 113 provided in the control unit 10, and the camera driving mechanism 113 scans and moves the imaging unit 13 in the horizontal plane (X-Y plane) along the lower surface of the microplate M held on the holder 11.

That is, in this embodiment, the imaging unit 13 can move and scan along the lower surface of the microplate M. Note that although the imaging unit 13 moves relative to the microplate M here, it is sufficient to realize a relative movement between the imaging unit 13 and the microplate M. In this sense, the microplate M may be moved relative to the imaging unit 13.

Image data obtained by the imaging unit 13 is fed to an image processor 114. The image processor 114 performs a suitable image processing to the image data from the imaging unit 13 and a predetermined arithmetic processing based on the image data. Data before and after the processing is saved and stored in a storage 115 if necessary.

This imaging apparatus 1 can be used in an application in which optical images of imaging targets such as a fluid or the like held in the respective wells W and cells and the like included therein are imaged and a peculiar part having a predetermined optical characteristic, more specifically an optical property different from the fluid or the like held in the wells W is detected from the optical image using a difference in its optical property. For example, it can be suitably used for the purpose of imaging cells or cell clumps (spheroids) being cultured in the culture medium as an imaging target and automatically detecting such cells and the like by further image processing. In this description, the "fluid and the like" is a collective term for fluids, gel-like or semi-fluid solid substances and substances that are, for example, poured into the wells in a fluid state and then solidified such as soft agar.

Figure 2A:
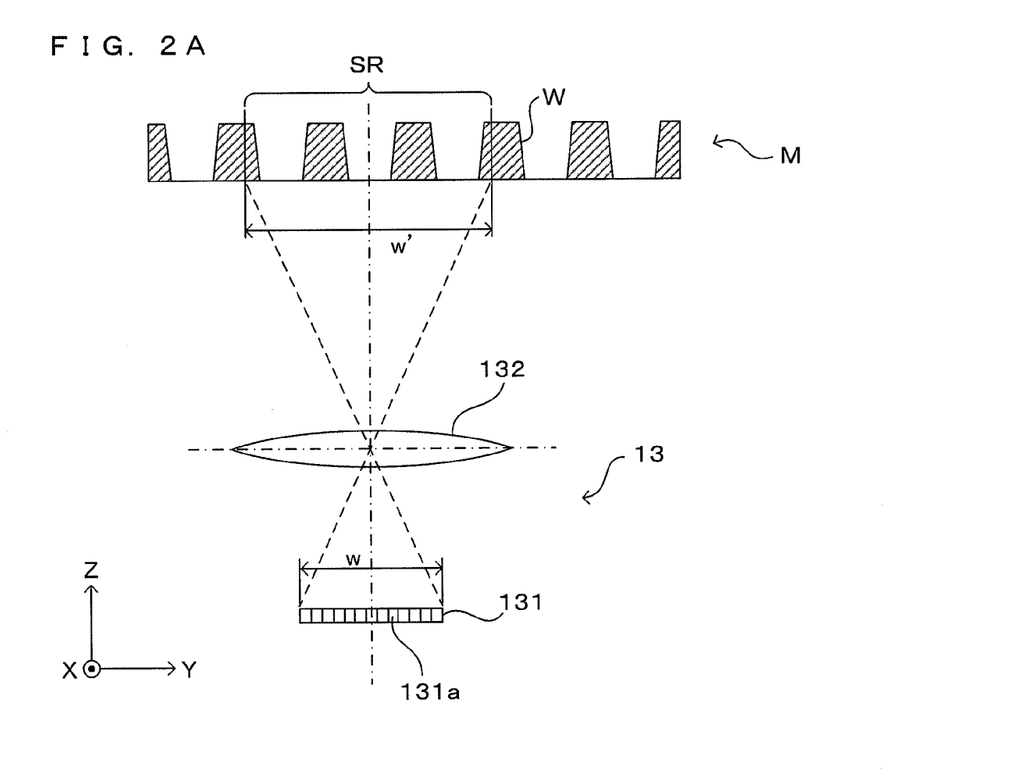
FIGS. 2A and 2B are drawings which show the more detailed structure of the imager part.
Figure 2B:
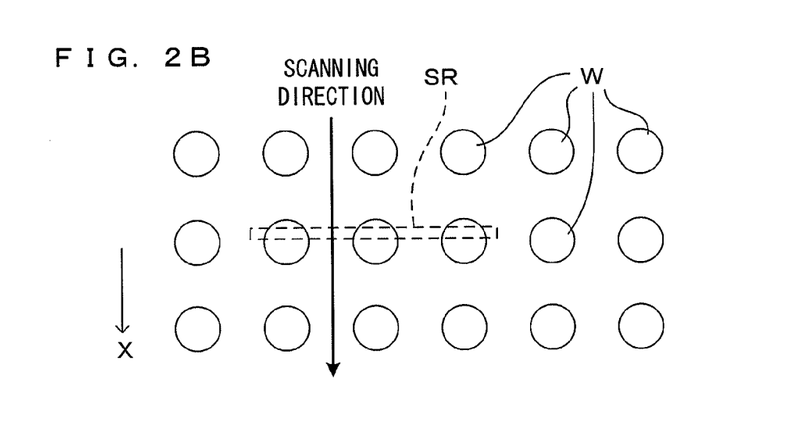

FIGS. 2A and 2B are drawings which show the more detailed structure of the imager part. As shown in FIG. 2A, the imaging unit 13 comprises a line sensor 131 formed by a CCD for instance which outputs an electric signal which is in accordance with incident light and an imaging optical system 132 which focuses, on a light receiving surface of the line sensor 131, light from the bottom surface of the microplate M which is held by the holder 11. While the imaging optical system 132 may comprise a plurality of optical components such as lenses, for the ease of understanding, FIGS. 2A and 2B show the imaging optical system 132 as one lens.

The line sensor 131 is formed by arranging a number of very small imaging elements 131a in one-dimensional arrangement, and is capable of covering, via the imaging optical system 132, at least one well W in its entirety, or more preferably, a plurality of wells W (three wells in FIGS. 2A and 2B), within the scope of imaging SR along the longitudinal direction of the line sensor 131. In FIGS. 2A and 2B, the symbol w denotes the Y-direction length of the line sensor 131, whereas the symbol w' denotes the Y-direction length of the field of view realized by the line sensor 131 at the bottom surface of the microplate M.

Further, as shown in FIG. 2B, the scanning direction of the line sensor 131 driven by the camera driving mechanism 113 is the X-direction. As the line sensor 131 in which the imaging elements are arranged in the Y-direction moves in a scanning motion in the X-direction along the bottom surface of the microplate M, a two-dimensional image of the microplate M as viewed from the bottom surface is captured. In addition, when the scanning motion above is repeated while changing the Y-direction position of the line sensor 131, the number of wells W formed in the microplate M can be imaged one after another.

Since each imaging element of the line sensor 131 has a small pixel size, it is possible to obtain high-resolution images. Further, these many imaging elements are arranged in a line-like arrangement, the imaging optical system 132 is configured such that the imaging elements form optical images of the respective sections of the wells W and the imaging elements are located appropriately so that light from one well or more than one wells impinges upon the line sensor 131. This shortens the time which is necessary to perform imaging of one well W. It is thus possible to perform imaging of the number of wells W at a high speed.

Figure 3A:
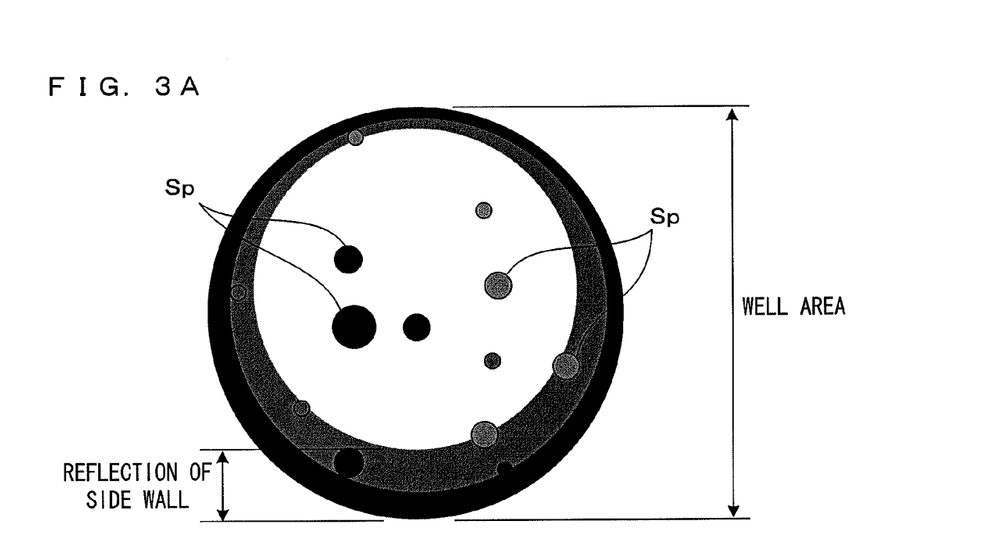
FIGS. 3A and 3B are drawings which show an imaging result example of one well.

FIGS. 3A and 3B are drawings which show an imaging result example of one well. As described above, in this embodiment, light is allowed to impinge from above the well W, and imaging is realized as light transmitted by the bottom surface of the well W toward below is received. Further, the line sensor 131 holds one well or more than one wells W as a whole within the scope of imaging. In this condition, the shadow of the side wall of the well W, and particularly, the shadow of the side wall of the well W above the surface of the fluid in the well W may appear as reflection within a well area of an image which corresponds to the well W because of the influence of refraction by the meniscus created by the fluid surface as shown in FIG. 3A. The influence is significant particularly when the side wall of the well is made of an opaque material. When the shadow like this comes on top of the image of cell clumps Sp, namely, a detection target, the cell clumps Sp may get concealed and the detection accuracy may deteriorate.

Figure 3B:
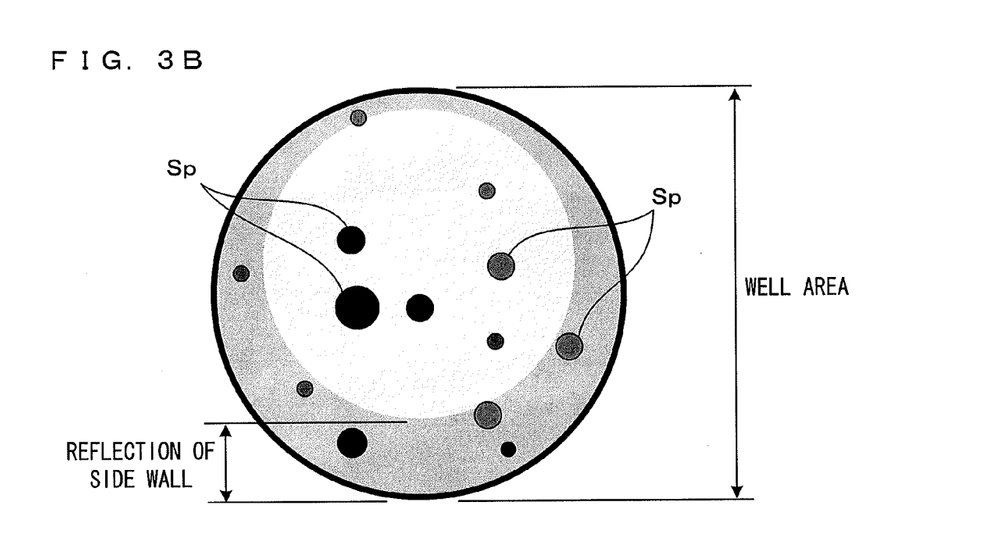

When respective sections inside the well area need be imaged microscopically, elimination of the shadow's influence as described above is relatively easy according to the patent document mentioned above (U.S. Pat. No. 7,718,131) for example. However, an imaging method like the one according to this patent document requires long time for imaging of the entire well area. To solve the problem, this embodiment does not require perfect exclusion of reflection of the side wall of the well into an imaging result. Instead, as shown in FIG. 3B, the embodiment requires the following in an attempt to reduce the influence of the shadow of the side wall of the well only to an extent not obstructing detection of the detection target such as the cell clumps Sp for instance.

Figure 4:
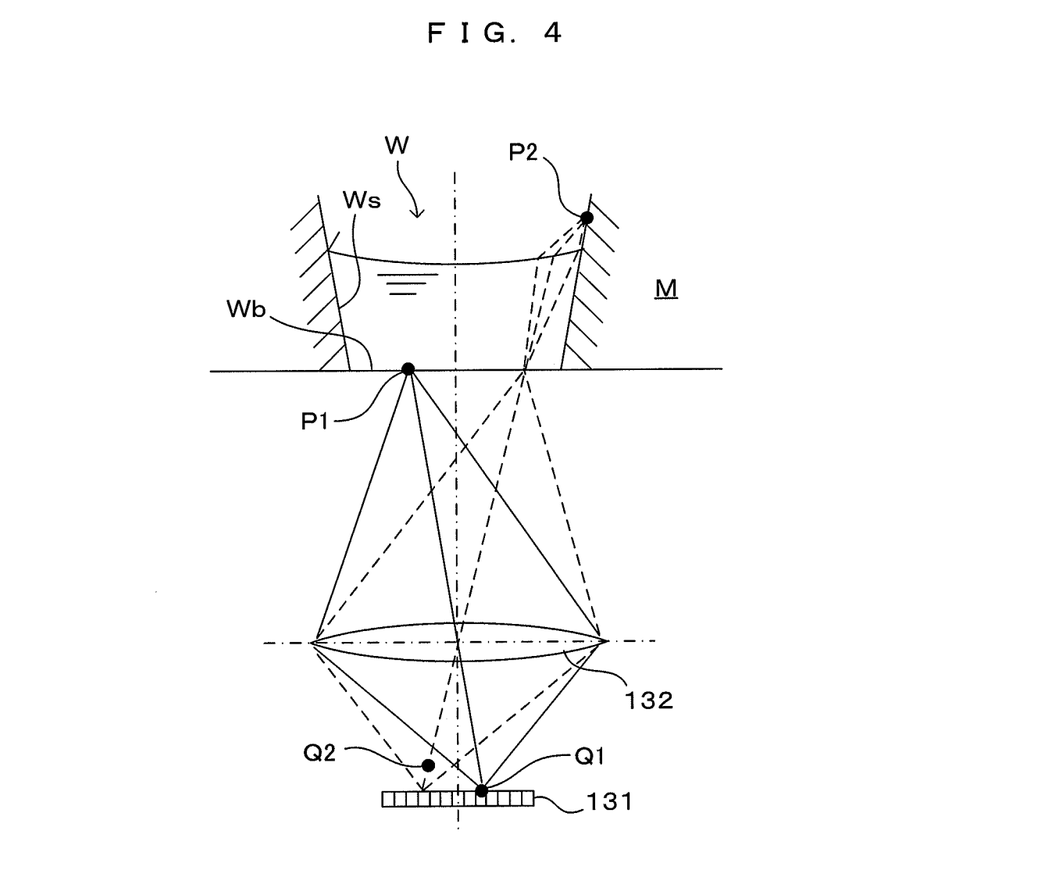
FIG. 4 is a drawing which illustrates the phenomenon that the shadow of the side wall of the well appears as reflection in the image.

FIG. 4 is a drawing which illustrates the phenomenon that the shadow of the side wall of the well appears as reflection in the image. First, as for an image of one point P1 within the bottom surface Wb of the well W, the imaging optical system 132 forms the image on the light receiving surface of the line sensor 131. In other words, parameters regarding the imaging optical system 132 and the relationship of the position among the imaging optical system 132, the microplate M and the line sensor 131 are set so that the image plane for the image which corresponds to the bottom surface Wb of the well coincides with the light receiving surface of the imaging elements 131. In FIG. 4, the symbol Q1 denotes a conjugate point for the point P1 via the optical system 132.

Meanwhile, outgoing light from one point P2 on the side wall Ws of the well above the surface of the fluid is refracted by the meniscus created by the surface of the fluid and is then imaged at a conjugate point Q2 via the optical system 132. When this image is projected upon the light receiving surface of the imaging elements in the line sensor 131, the side wall Ws of the well appears as reflection in the imaging result. In the event that the light from the side wall Ws of the well is out of focus at the light receiving surface of the line sensor 131, the reflection of the side wall Ws of the well is blurred. The inventors of the invention have conceived reduction of the influence exerted by the side wall Ws of the well upon the imaging result while utilizing this. More specifically, with the depth of field of the imaging optical system 132 set appropriately based upon the principle above, the influence exerted by the side wall Ws of the well upon the imaging result is reduced. Consideration to realize this and the result of the same will now be described.

Figure 5A:
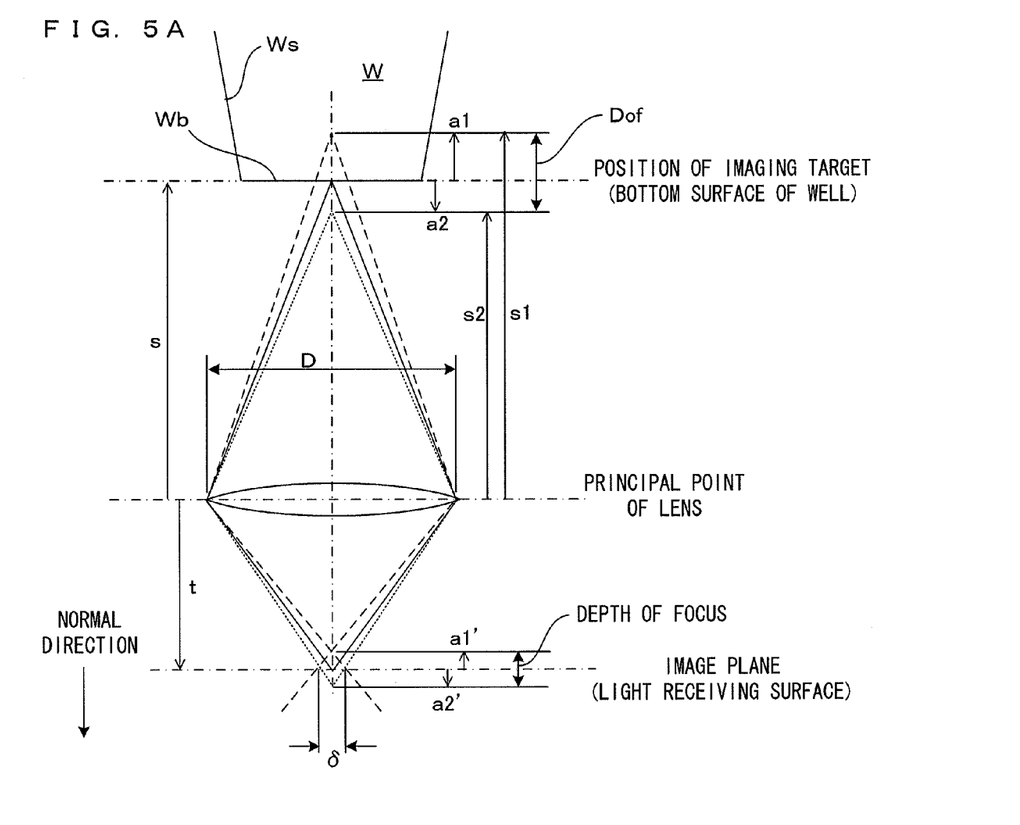
FIGS. 5A and 5B are drawings which show how the depth of field is related to the sizes of the respective sections.
Figure 5B:
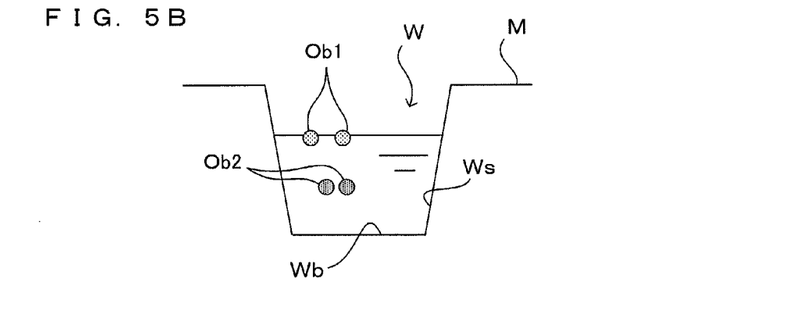

FIGS. 5A and 5B are drawings which show how the depth of field is related to the sizes of the respective sections. In more specific words, FIG. 5A is a drawing which shows the sizes of the respective sections on the assumption that an imaging target near the bottom surface of the well is imaged. FIG. 5B is a drawing which shows other example of a distribution of imaging targets. The symbols appearing in FIG. 5A respectively show the following.

s: the distance between the principal point of the lens and the imaging target (i.e., the bottom surface Wb of the well)

t: the distance between the principal point of the lens and the light receiving surface of the line sensor 131

D: the effective diameter of the lens (the diameter of the effective flux of the incident beam impinging over an infinite distance)

f: the focal length $|a1'|$: the rear-side depth of focus $|a2'|$: the front-side depth of focus Dof: the depth of field ($=a2-a1$)

$|a1|$: the rear-side depth of field $|a2|$: the front-side depth of field s1: the distance between the principal point of the lens and the rear-side end of the depth of field s2: the distance between the principal point of the lens and the front-side end of the depth of field As shown in FIG. 5B, in the event that the imaging target is an object Ob1 which is near the surface of the fluid or the like or an object Ob2 which is inside the fluid or the like, while adjusting the optical system such that the imaging target comes into focus, the concept below can be applied with the distance between the principal point of the lens and the imaging target (to be more exact, the horizontal surface which includes the imaging target) substituted with the distance s as defined above. A situation that the imaging target is inside the fluid or the like may for example be a situation that the culture medium and the imaging target are not greatly different from each other in terms of specific gravity, a situation that after the culture medium such as soft agar is laid thin inside the well W, cells or the like are then cultured on the culture medium, a further culture medium is injected and sealed (embedded culture), etc.

In FIGS. 5A and 5B, the normal direction is the downward direction, and the sizes denoted at one-directional arrows are expressed with the signs which correspond to the normal and the opposite directions. That is, the sizes denoted at the downward one-directional arrows take positive values, while those denoted at the upward one-directional arrows take negative values. The plus and the minus signs of the respective values have been taken into consideration in the formulae below.

While the symbol δ in FIGS. 5A and 5B is indicative of the diameter of the circle of confusion created by the imaging optical system 132, for the purpose of obtaining a high-resolution image while making a maximum use of the resolution power of the line sensor 131, it is ideal that the permissive value of the diameter of the circle of confusion, namely, the size of the permissible circle of confusion is about the same as the pitch between the imaging elements which are arranged in the line sensor 131. Denoted at the symbol δ is the size of the permissible circle of confusion which meets this condition.

The formula for calculating the depth of field Dof is derived as described below while considering the signs which appear in FIGS. 5A and 5B. An equation can be expressed as described below from the definition of the F-number of the lens ($F=f/D$) and the relationship of similarity shown in FIGS. 5A and 5B.

$$a'_1 = -\frac{\delta Ft}{(f+\delta F)}$$

$$a'_2 = \frac{\delta Ft}{(f-\delta F)}$$

Further, the equation can be expressed as described below from the Gaussian lens formula:

$$(1/t)-(1/s)=1/f$$

$$t = \frac{fs}{(f+s)}$$

$$\frac{1}{(t+a'_1)} - \frac{1}{s_1} = \frac{1}{f}$$

$$\frac{1}{(t+a'_2)} - \frac{1}{s_2} = \frac{1}{f}$$

Removing a1' and a2' from these equation and rewriting these with s1 and s2, the following is obtained.

$$s_1 = s + a_1 = \frac{sf^2}{f^2 + (f+s)\delta F}$$

$$s_2 = s + a_2 = \frac{sf^2}{f^2 - (f+s)\delta F}$$

The depth of field Dof can therefore be expressed by the formula below.

$$Dof = s_2 - s_1 = \frac{sf^2}{f^2 - (f+s)\delta F} - \frac{sf^2}{f^2 + (f+s)\delta F} = \frac{2sf^2 \delta F(f+s)}{f^4 - \delta^2 F^2(f+s)^2}$$

A preferable range of the depth of field for attaining the purpose of reducing the influence of reflection exerted by the side wall of the well will now be described. The experiment which the inventors of the invention conducted is as described below. A grid chart having a matrix arrangement of a number of equidistant dots was adhered to the bottom surface of the microplate which had 96 holes. Alcohol was introduced into these wells in the quantity of 100 micro liters, a quantity of the culture fluid which is generally used, and imaging was performed using the imaging apparatus 1 which is shown in FIG. 1A. At that stage, how well the dots on the grid chart were detected was calculated from the imaging result. The resolution power of the imaging unit 13 was 2400 dpi.

In the medical and life science fields to which the imaging apparatus 1 is applicable, in an attempt to assist a user, a captured image is subjected to image processing which is for automatic measurement of the concentration, the area size, the count or the like of cells or cell clumps. The experiment intended to identify a condition under which such processing is simulated and reproduced and a favorable detection accuracy is ensured.

Figure 6A:
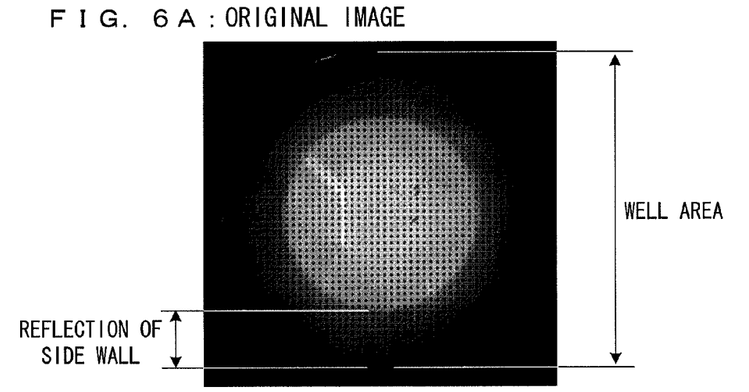
FIGS. 6A through 6C are drawings which show a test result example.
Figure 6B:
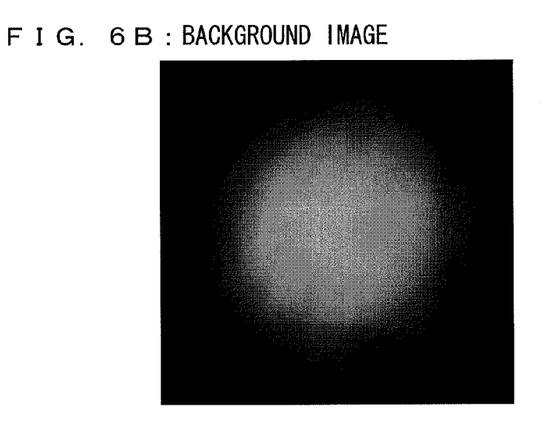
Figure 6C:
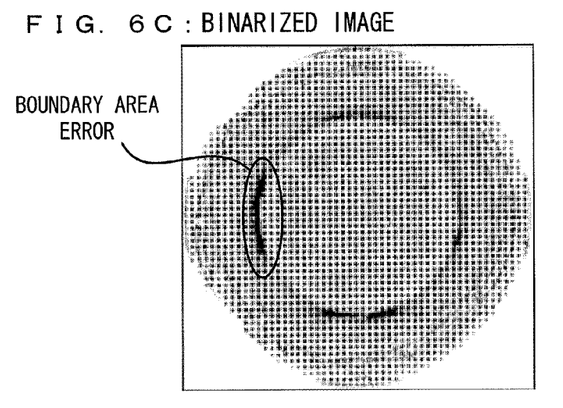
Figure 7:
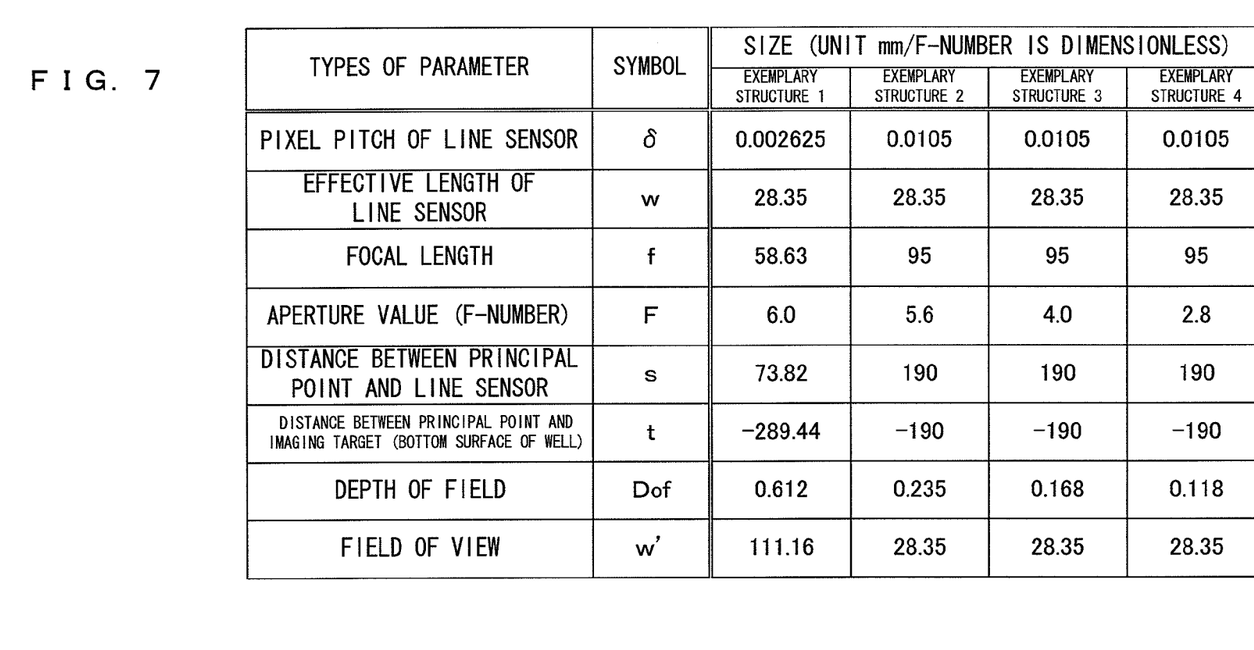
FIG. 7 is a drawing which shows an example of the structure of the optical system used for the experiment.

FIGS. 6A through 6C are drawings which show a test result example. FIG. 7 is a drawing which shows an example of the structure of the optical system used for the experiment. As shown in FIG. 6A, an original image which was captured includes many of the dots of the grid chart. Although the contrast is clear between the high-luminance background at the center of the well area and lower-luminance dots, reflection of the side wall of the well becomes more apparent with a distance toward the periphery of the well area, thereby reducing the contrast between the dots and the background.

What is generally used as a method of detecting low-luminance areas, such as the dots of the grid chart, from an image in which the luminance locally changes is a method which requires smoothing the original image and accordingly creating a background image (FIG. 6B), then subtracting the background image from the original image pixel by pixel, and binarizing the image using an appropriate threshold value.

However, while the contrast difference is small between the dots and the background in the peripheral portion of the well area, the luminance greatly changes at the boundary between the peripheral area, in which reflection of the side wall of the well appears, and the central portion without such reflection. Hence, as a result of binarization, something which is not a detection target may be detected, e.g., the sections indicated as "BOUNDARY AREA ERROR" in FIG. 6C. The greater the local luminance change is, the greater the degree of smoothing is, and the smaller the binarized threshold value is, the more easily such a detection error occurs.

The boundary area detection errors in FIG. 6C occur in the boundary area between the central portion and the peripheral area which is affected by reflection of the side wall of the well. The errors can be eliminated when the depth of field Dof of the imaging optical system 132 is reduced and the luminance change in the boundary area is accordingly eased. Noting this, an experiment was conducted to quantitatively examine the relationship between the depth of field and boundary area errors.

In the experiment, using similar samples to the sample described above, imaging was performed using a plurality types of optical systems having different depths of field from each other, and the frequency of losses (i.e., the number of undetected dots) due to boundary area errors was measured. The depths of field which were used were 612 μm, 235 μm, 168 μm and 118 μm for instance. The exemplary structures of these optical systems are as shown in FIG. 7. A mean filter was used as the smoothing method, and the filter size was set at 50 pixels, namely, a size with which cells or cell clumps can be detected at an adequate accuracy. This is based upon the experimentally gathered findings that the average size is approximately 30 pixels in the case of imaging cells or cell clumps which are detection targets with this apparatus at resolution power of 2400 dpi.

After smoothing and binarization, filtering based upon the roundness is performed on each one of detected areas which were detected as they had a predetermined luminance value. Those having the roundness of less than 0.4 were determined to be something other than the dots which were detection targets, and their occurrence frequency was counted as the error frequency.

The measurement based upon the captured image data was executed a plurality of times for each one of the depths of field while changing the binarized threshold value, the final detection error count was determined to be the average value obtained from the three largest binarized threshold values (which are considered to be appropriate thresholds) in order of the dot detection count for the entire well area. Further, the ratio of the error count to the total dot count was calculated.

Figure 8A:
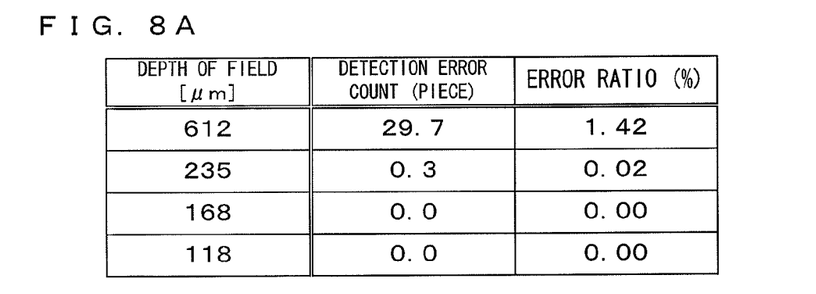
FIGS. 8A and 8B are drawings which show a typical test result example.
Figure 8B:
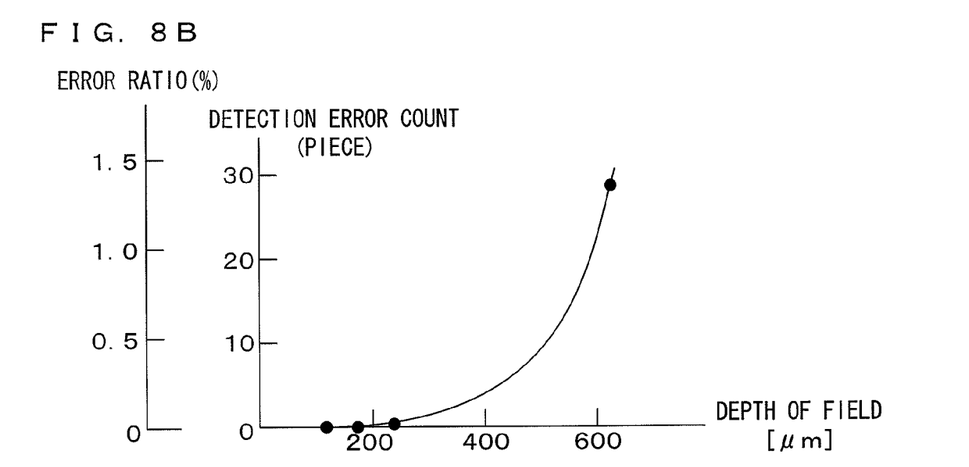

FIGS. 8A and 8B are drawings which show a typical test result example. FIG. 8A is a table which shows the result of the measurement above, and FIG. 8B is a graph of the same. As shown in FIGS. 8A and 8B, when the depth of field is reduced, errors can be reduced. The equation below well approximates the detection error count:

$$y=0.000151111x^2-0.050516x+3.9809 \quad \text{(Equation 1)}$$

Meanwhile, the ratio of the detection errors is well approximated by the equation below:

$$y=0.000007251x^2-0.002424x+0.19102 \quad \text{(Equation 2)}$$

For prevention of detection errors for instance, (Equation 1) may be solved with respect to x using y=1, and the depth of field may accordingly be set to 257.8 μm or less. In the meantime, when the detection error ratio is desired to be 1% or smaller for instance, (Equation 2) may be solved with respect to x using y=1, and the depth of field may accordingly be set to 540.7 μm or less.

The influence of conditions for the imaging above will now be studied. As for differences of the fluid quantities held inside the wells, while the width of the range representing the influence of the side walls of the wells in the well areas changes due to the differences, since the relationship between the physical position of the optical system and that of the top ends of the wells stays unchanged, the luminance level changes in the boundary areas are not different from each other. The result above is therefore not affected.

With respect to the resolution power of the imaging unit 13, since the resolution power changes the pixel count corresponding to the size of a detection target (cell clump), it may become necessary in some instances to change the size of the mean filter in order to secure an adequate detection accuracy. However, the local luminance changes in the areas with the boundary area errors as well vary similarly, the correlation between the depth of field and the errors is maintained.

It then follows that when the depth of field is approximately 0.6 mm or smaller, in a condition that the binarized threshold value is appropriately set, the detection errors due to the influence of reflection of the side walls of the wells can be reduced down to 1% or less or down to substantially zero. According to this embodiment, the depth of field of the imaging optical system 132 which makes the imaging elements focus the transmitted light which is transmitted by the bottom surface of the microplate toward below is set properly, whereby the influence of the side walls of the wells is suppressed and high-resolution images are captured. Further, even in a state that one well area or more than one well areas are contained within the scope of imaging (In FIG. 7, each one of the "FIELD OF VIEW w'" values is three times as large as or larger than the well arrangement pitch Dp.), it is possible to suppress the influence of the side walls of the wells. Hence, it is possible to shorten the time required for imaging per well. This makes it possible to perform imaging of each well at a high measurement accuracy and at a high speed. Further, based upon thus captured images, it is possible to accurately detect a clump-like object to be detected such as a cell clump.

While microplates and wells of various sizes may be used, using the sizes of the respective sections and the parameters regarding the line sensor 131 and the imaging optical system 132 which are appropriately combined with each other as shown in FIG. 7 for example, it is possible to capture images which are less influenced by the side walls of the wells while performing efficient imaging of the plurality of wells on any desired microplate.

As described above, in this embodiment, the light source 12 functions as the "illumination member" of the invention, while the imaging unit 13 functions as the "imager member" of the invention. The imaging optical system 132 functions as the "optical system" of the invention. Meanwhile, the camera driving mechanism 113 functions as the "mover mechanism" of the invention. In addition, the microplate M corresponds to the "sample plate" of the invention according to the embodiment.

The invention is not limited to the embodiment described above but may be modified in various manners in addition to the embodiments above, to the extent not deviating from the object of the invention. For instance, the embodiment above is directed to an imaging apparatus for imaging wells which are formed in a microplate. However, as the image processor 114 executes appropriate detection processing algorithm for extracting predetermined characteristics portions based upon captured image data, the imaging apparatus can serve as the "detecting apparatus" of the invention in addition to execution of imaging. In such an instance, the light source 12, the holder 11 and the imaging unit 13 function together as the "imager part" of the invention which is one of the components of the detecting apparatus, whereas the image processor 114 functions as the "detector part" of the invention.

Further, image data captured by the imaging apparatus according to the embodiment may be transmitted to an external detecting apparatus via predetermined interface, and the detecting apparatus may perform the detection processing.

Further for example, the embodiment above requires that the line sensor 131 formed by one-dimensional arrangement of the imaging elements moves relative to the microplate M. However, imaging may be performed using a CCD array in which imaging elements are arranged in a two-dimensional matrix.

Further, while the foregoing has described the embodiment as using one lens as the imaging optical system 132, this is not limiting. Even when an optical system formed by a plurality of optical components is used, it is possible to set the depth of field of the optical system based upon a similar concept to that according to the embodiment above.

In the imaging apparatus of the invention, for example, the imaging element may be a line sensor, and the imager member may comprise a mover mechanism which moves the optical system and the line sensor together as one unit relative to the sample plate along a bottom surface of the sample plate. Use of the line sensor makes it possible to acquire high-resolution images along one-dimensional direction, and as the line sensor moves relative to an imaging target, high-resolution two-dimensional images are obtained.

In that case for example, the depth of field may be defined by a following formula:

$$Dof=2sf^2\delta F(f+s)/\{f^4-\delta^2F^2(f+s)^2\},$$

where a symbol Dof denotes the depth of field, a symbol s denotes a distance between a principal point of the optical system and a bottom surface of the well, a symbol f denotes a focal length of the optical system as measured on the imaging element side, a symbol F denotes a F-number of the optical system, and a symbol δ denotes a pixel pitch of the line sensor.

Alternatively, the image plane at which the optical system forms the images corresponding to the bottom surfaces of the wells may coincide with a light receiving surface of the imaging element, i.e., the imager member focuses at the bottom surfaces of the wells. In this case, it is possible to clearly focus the images corresponding to the bottom surfaces of the wells at the light receiving surface of the imaging element and to capture high-resolution images while making a maximum use of the resolution power of the imaging element.

As described earlier, the invention is remarkably efficacious when the imager member is configured so as to capture images including a plurality of wells for instance. For imaging of a part of one well alone, only an area which is free from the shadow of the side wall of the well is brought into inside the scope of imaging and captured, it is possible to eliminate the influence of the shadow. However, during imaging of a plurality of wells all at once, reflection of the shadows of the side walls of the wells is inevitable, and therefore, the invention is particularly useful.

Further alternatively, the illumination member may be configured so as to irradiate the sample plate with white light. This type of imaging of a sample often uses a method which uses light having a limited wavelength such as ultraviolet light for instance and accordingly realizes fluorescence of a particular molecule. Meanwhile, it is possible according to the invention to perform imaging in the visible light range using white light, which provides a highly convenient environment for observation to a user at a low cost.

This invention can be particularly suitably applied to a technology for imaging a specimen holding plate including many wells such as a microplate at a high accuracy and at a high speed, for example, used in the medical and bioscience fields and detecting the density of a detection target, but its fields of application are not limited to the medical and bioscience fields.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. An imaging apparatus for imaging a sample plate whose surface has a plurality of wells which are capable of holding a fluid, comprising:
   an illumination member which irradiates light from above the sample plate which is in a horizontal condition; and
   an imager member which receives transmitted light which is transmitted to below the sample plate and captures an image which includes at least one of the wells,
   wherein the imager member includes an imaging element and an optical system which focuses the transmitted light upon the imaging element, and a depth of field of the optical system is equal or smaller than 0.6 mm;
   wherein the depth of field is defined by a following formula:

$$Dof=2sf^2\delta F(f+s)/\{f^4-\delta^2 F^2(f+s)^2\}$$

where a symbol Dof denotes the depth of field, a symbol s denotes a distance between a principal point of the optical system and a bottom surface of the well, a symbol f denotes a focal length of the optical system as measured on the imaging element side, a symbol F denotes a F-number of the optical system, and a symbol δ denotes a pixel pitch of the imaging element.

2. The imaging apparatus of claim 1, wherein the imaging element is a line sensor, and the imager member comprises a mover mechanism which moves the optical system and the line sensor together as one unit relative to the sample plate along a bottom surface of the sample plate.

3. The imaging apparatus of claim 1, wherein an image plane at which an image corresponding to the bottom surface of the well is imaged by the optical system coincides with a light receiving surface of the imaging element.

4. The imaging apparatus of claim 1, wherein the imager member captures an image which contains the plurality of wells.

5. The imaging apparatus of claim 1, wherein the illumination member irradiates white light upon the sample plate.

6. A detecting apparatus, comprising:
   an imager part which has a same structure as that of the imaging apparatus of claim 1; and
   a detector part which detects a specific section, which is contained in a liquid-state or solid-state culture medium which is held in the well and which exhibits a different optical characteristic from a culture medium, based upon an image captured by the imager part.

7. An imaging method of imaging a sample plate which has a plurality of wells which hold a liquid-state or solid-state culture medium, comprising the steps of:
   irradiating light from above the sample plate which is in a horizontal condition; and
   capturing an image containing at least one of the wells by an imaging element while the optical system focuses a light transmitted to below the sample plate upon the imaging element, wherein
   a depth of field of the optical system is equal to or smaller than 0.6 mm,
   wherein the depth of field is defined by a following formula:

$$Dof=2sf^2\delta F(f+s)/\{f^4-\delta^2 F^2(f+s)^2\}$$

where a symbol Dof denotes the depth of field, a symbol s denotes a distance between a principal point of the optical system and a bottom surface of the well, a symbol f denotes a focal length of the optical system as measured on the imaging element side, a symbol F denotes a F-number of the optical system, and a symbol δ denotes a pixel pitch of the imaging element.

8. The imaging method of claim 7, wherein an image plane at which an image corresponding to the bottom surface of the well is imaged by the optical system coincides with a light receiving surface of the imaging element.

* * * * *